Figure 4A:
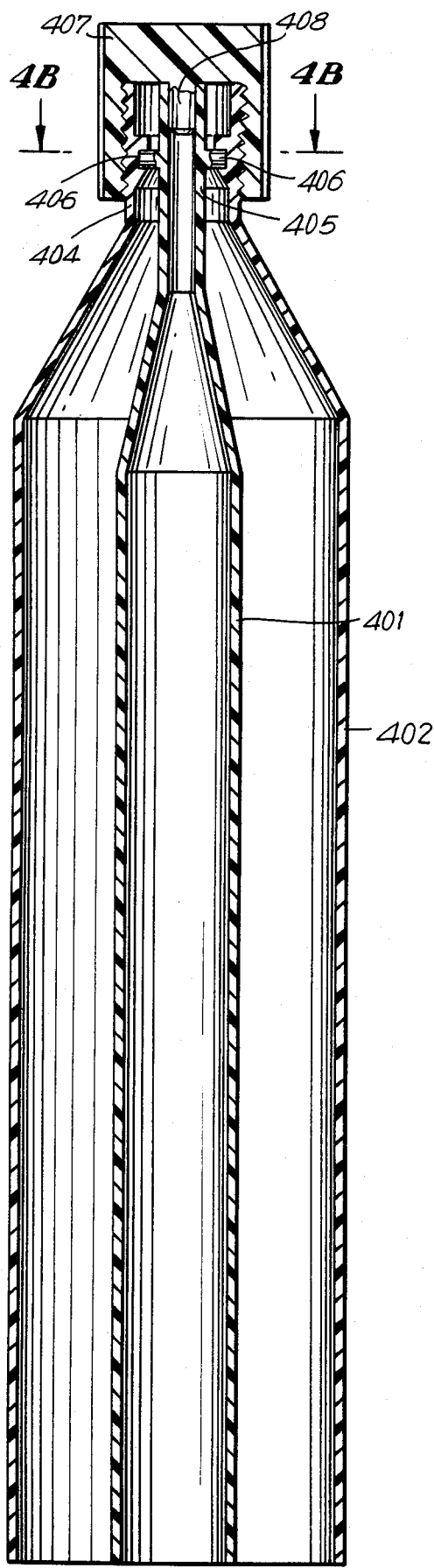

United States Patent [19]
Schaeffer

[11] Patent Number: 4,687,663
[45] Date of Patent: Aug. 18, 1987

[54] DENTAL PREPARATION, ARTICLE AND METHOD FOR STORAGE AND DELIVERY THEREOF

[76] Inventor: Hans A. Schaeffer, 18 Pallant Ave., Linden, N.J. 07036

[21] Appl. No.: 745,993

[22] Filed: Jun. 17, 1985

Related U.S. Application Data

[63] Continuation-in-part of Ser. No. 737,157, May 23, 1985, abandoned, which is a continuation-in-part of Ser. No. 471,188, Mar. 1, 1983, Pat. No. 4,528,180.

[51] Int. Cl.4 .......................... A61K 7/16; A61K 7/18; A61K 7/20
[52] U.S. Cl. ......................................... 424/52; 424/49; 424/53; 514/835; 514/900; 514/902; 514/944; 222/1; 222/94
[58] Field of Search ................. 222/1, 94; 424/49, 52, 424/53; 514/835, 900, 902, 944

[56] References Cited

U.S. PATENT DOCUMENTS

| | | | |
|---|---|---|---|
| 2,905,364 | 9/1959 | Marrafino | 222/94 |
| 2,914,220 | 11/1959 | Marrafino | 222/94 |
| 3,175,731 | 3/1965 | Ellman | 222/94 |
| 4,528,180 | 7/1985 | Schaeffer | 424/52 |

Primary Examiner—Shep K. Rose
Attorney, Agent, or Firm—Darby & Darby

[57] ABSTRACT

Disclosed is a method for cleaning teeth including extruding a first semi-solid component including hydrogen peroxide as an active ingredient, and extruding a second semi-solid component comprising sodium bicarbonate as an active ingredient, the first and second components being suitable for oral use. The first component and the second component are placed in contact with each other on a toothbrush. The teeth are brushed using the first and second components concurrently as a cleaning medium.

17 Claims, 7 Drawing Figures

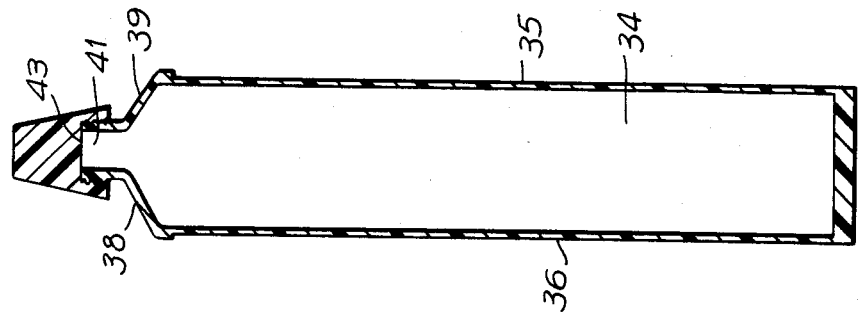
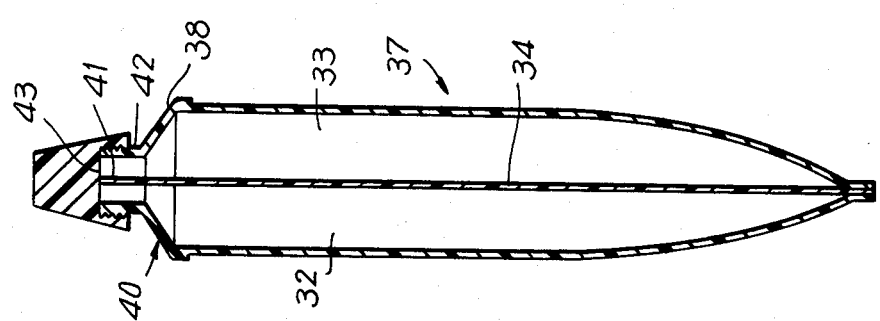
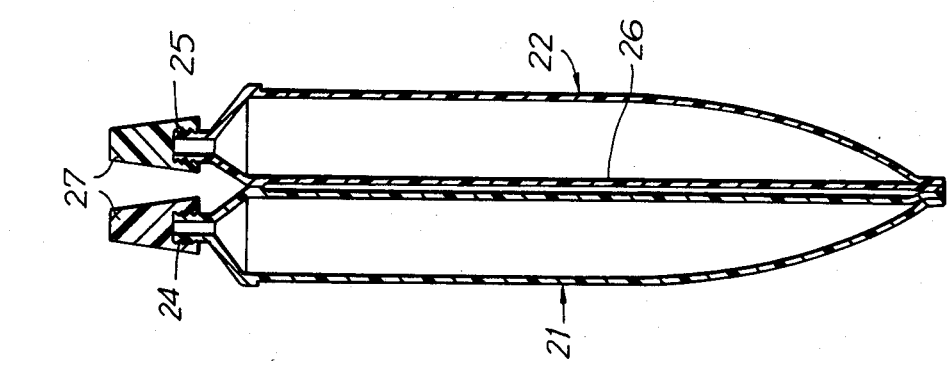
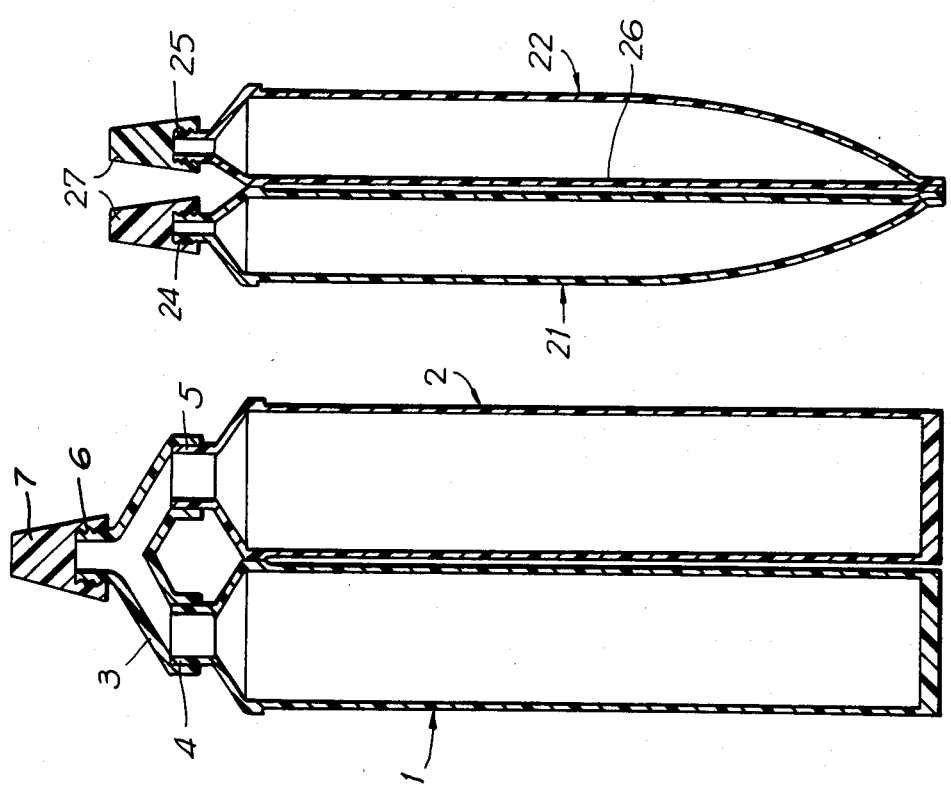

DENTAL PREPARATION, ARTICLE AND METHOD FOR STORAGE AND DELIVERY THEREOF

This is a continuation-in-part, of application Ser. No. 737,157 filed 5/23/85, abandoned which in turn is a continuation-in-part of appln. Ser. No. 471,188, filed 3/1/83 now U.S. Pat. No. 4,528,180.

This invention relates to a dental preparation useful in the treatment of gum disease, to a method of storing and delivering such preparation to a use point and to an article for the storage and delivery of such preparation.

It has long been recognized that the combination of hydrogen peroxide solution with sodium bicarbonate and table salt has an excellent curative and preventive effect on gum disease caused by bacterial infection. Dr. Paul H. Keyes has advocated use of this combination to the dental profession and to the public at large based on his work of more than 25 years on the subject, which has shown that upon daily and diligent topical application of these materials, gum disease may be effectively controlled. On the basis of his recommendations, many dentists urge their patients to use the Keyes procedure (substantially as described e.g. in S. Elder: "An Alternative To Gum Surgery" Modern Maturity, August–September 1980 pp. 31–32).

Dr. Keyes advocates that a quantity of solid sodium bicarbonate be placed in one hand, and that the toothbrush, held in the other hand, be dipped into a hydrogen peroxide-table salt solution and then transferred to the bicarbonate and applied to the teeth and gums. Upon contact with the gums, the hydrogen peroxide is exposed to the enzyme catalase, which is always present in the buccal cavity, and is attacked thereby resulting in the release of active oxygen. The combination of the active oxygen and the sodium bicarbonate together with table salt destroys the bacteria responsible for gum desease. Unfortunately, hydrogen peroxide and sodium bicarbonate may not be premixed, as they immediately react and are thereby rendered ineffective against gum desease. In addition, hydrogen peroxide is unstable and therefore difficult to store for prolonged periods of time. Finally, mere dipping of the toothbrush in a hydrogen peroxide solution does not insure delivery of a sufficient amount of hydrogen peroxide to the teeth and gums. These factors are responsible for the fact that use of the Keyes procedure is extremely awkward, inconvenient and messy. Another disadvantage stems from the fact that, the mixture of hydrogen peroxide and sodium bicarbonate has a very unpleasant taste. For these reasons, patients have shown extreme reluctance to follow this procedure, especially on a daily basis, as would be required for effective gum desease control. As a result, the benefits which the Keyes procedure affords have largely been left unrealized.

Accordingly, it is an object of this invention to eliminate the above disadvantages associated with use of the Keyes procedure by providing a dental preparation incorporating the active constituents of the Keyes procedure that has pleasant taste and is neat and convenient to use, and a method for using such preparation that permits contact between hydrogen peroxide and sodium bicarbonate only shortly before use and, therefore, assures maximum effectiveness against gum disease.

It is another object of the present invention to provide a dental preparation incorporating the active constituents of the Keyes method and a method for using such preparation that permits a sufficient, consistent and reproducible amount of hydrogen peroxide to be delivered to the use point.

It is yet another object of this invention to provide an article for the storage and delivery of this improved dental preparation which makes its use neat and convenient and which prevents contact between hydrogen peroxide and sodium bicarbonate prior to application.

In accordance with the present invention, hydrogen or urea peroxide is dissolved in a nontoxic gel for use in combination with a separately stored but substantially simultaneously dispensed paste containing sodium bicarbonate, table (or another suitable) salt, and, preferably, additional cleansing, anticaries and polishing agents as well as an effective concentration of flavoring substances. Each of the gel and paste are loaded either into separate collapsible containers which are connected by means of a common orifice (as in FIG. 1), or which have substantially adjacent orifices (as in FIG. 2), or in separate compartments of a single container (as in FIGS. 3 or 4). Alternatively, the gel and paste may be loaded in separate compartments of a two-compartment pressurized container (as in FIG. 5) or a mechanically actuated pump, as in FIG. 6.

Upon substantially simultaneous squeezing of the containers, in much the same way as common toothpaste tubes (or upon actuating of the pressurized container or pump), controlled quantities of the gel and paste can be simultaneously released onto the toothbrush and immediately applied to the teeth and gums. Control of the peroxide, salt, and $NaHCO_3$ quantities delivered may be thus effected by specification of the opening of the orifice and the active ingredient concentration in each tube (or pump compartment). As described above, when the brush is applied to teeth and gums, immediate mixing of the products takes place followed by the rapid evolution of active oxygen and carbon dioxide. At the same time, the effervescence accompanying release of active oxygen activates the flavor contained in the bicarbonate paste and produces a lasting highly refreshing taste in the mouth which is unlike any other flavor provided by existing toothpastes or gels.

Another advantage afforded by the present invention, as compared with the Keyes procedure, is that a greater and more consistent amount of peroxide is delivered to the use point.

Yet another advantage stems from the tendency of the present composition to cling to the gum tissues and thus provide them with the full benefit of substantially all of the composition applied to the gums.

Gelling agents suitable for use in preparation of the peroxide gel in accordance with this invention should be nontoxic and neutral to the peroxide to assure its stability. In addition, they should be preferably sensitive to external electrolytes, such as those contained in the sodium bicarbonate paste, in order to make peroxide immediately available to the oral tissues. A gelling agent suitable for use with the present invention is a copolymer of acrylic acid cross-linked with polyallyl sucrose, as described in U.S. Pat. No. 2,798,053 issued on July 2, 1957 and assigned to B. F. Goodrich Inc. Other gelling agents resulting in stable hydrogen (or urea) peroxide gels suitable for use in the present invention include those described in British Pat. No. 827,331, i.e., organic polymeric acid colloids including polyuronic acids, carboxypolymethylene compounds and polyester resins containing three carboxyl groups, such as partially hydrolized polyacrylates or polymethacrylates and copolymers thereof; and those described in U.S. Pat. No. 3,639,574 issued on Feb. 1, 1972 to Schmolka, i.e., polyoxyethylene polyoxypropylene block copolymers, which, according to Schmolka, may be used in the preparation of stable, firm hydrogen peroxide gels. Preferred are water-dispersible copolymers of acrylic acid cross-linked with about 0.75 to about 1.5% of polyallyl sucrose and neutralized with triethanolamine, NaOH or another alkalizing agent, as taught in U.S. Pat. No. 3,499,844[1] issued on Mar. 10, 1970 to Kibbel et al. For purposes of the present invention, Kibbel's acrylic copolymer may be preferably combined with an anionic or non-ionic surfactant, such as disclosed in U.S. Pat. No. 4,130,501[2] issued on Dec. 19, 1978 to Lutz et al. Such surfactants are not essential for the formation of a stable hydrogen peroxide gel in accordance with this invention, but may be added to facilitate distribution and rapid penetration of the active oxygen throughout the area to be treated. A particularly preferred gelling agent for the purposes of the present invention is that described by Kibbel, supra. This gelling agent may but does not have to be modified by the addition of a suitable amount of non-ionic cellulose gum such as hydroxyethyl- or hydroxypropyl-cellulose or hydroxypropyl-methyl-cellulose in order to improve the physical stability of the gel, especially when subjecting it to stress such as that resulting from squeezing of the collapsible tubes, or pumping action.

[1]The disclosures of these patents are incorporated herein by reference.
[2]The disclosures of these patents are incorporated herein by reference.

The most preferred gelling agents are marketed under the trademark CARBOPOL 941 or 1342 by Goodrich. Carbopol 941 does not need neutralization for gelling (and preferably is not neutralized in this invention) because it gels readily in the presence of hydrogen donors. Carbopol 941 has proved to have greater long term physical stability (also believed to be due to hydrogen bonding). Although Carbopol 1342 has just become available on the market and its composition and characteristics have not been fully disclosed, it is claimed by the manufacturer that this acrylic acid copolymer (even though it needs to be neutralized) displays satisfactory long term stability comparable to that of Carbopol 941.

Gels made from these agents do not need any cellulose additive as a stabilizer, because they are thixotropic (and also pseudoplastic).

Not only is Carbopol 941 the most preferred gelling agent for non-neutralized gels, it is also most preferred for neutralized gels along with Carbopol 934, 940 and 1342.

The hydrogen peroxide gel may then contain the following ingredients in the following amounts—$H_2O_2$: about 0.1–10.0% and preferably about 3.0–6.5%; Acrylic acid copolymer: about 0.05–5.0% and, preferably, about 1.0–3.0%; nonionic cellulose gum (optional): about 0–2.0% and, preferably, about 0.3–1.5%; neutralizing agent (triethanolamine, diisopropanolamine, NaOH, KOH): an amount sufficient to raise the gel pH to about 3.0–6.0; NaOH is preferred. The balance is purified (distilled or deionized) water.

If a non-neutralized gelling agent is used, the aforementioned gel may contain about 2–80% and preferably about 20–60% by weight of a polyol selected from the group consisting of glycerin, sorbitol (70% solution) polypropylene glycol, propylene glycol, polyethylene glycol, ethoxylated or propoxylated lower ($C_2$–$C_5$) fatty alcohols and mixtures thereof. The preferred polyol is glycerin. The amount of the water is decreased so that the total adds up to 100% by weight. The pH need not be controlled but falls between about 2 and 4.

The sodium bicarbonate paste contains sodium bicarbonate, sodium chloride (or another suitable salt although the salt may be omitted, if desired), purified (distilled or deionized) water, a thickener/stabilizer such as cellulose gum and or magnesium-aluminum silicate, as essential ingredients and, most preferably, it also contains a polishing/stabilizing agent, such as bentonite, silica, titanium dioxide, magnesium oxide or mixtures thereof (the first three and their mixtures are preferred). In order to disperse the "chalky" taste imparted mostly by the bicarbonate and enhance the taste and plasticity of the paste, a bodying agent is added, such as sorbitol, glycerin and/or a glycol. In addition, if the paste (in combination with the gel) is to displace toothpaste completely, additional cleansing agents, such as calcium sulfate, calcium phosphate, hydrated aluminum oxide, calcium carbonate, magnesium carbonate, and magnesium silicate or mixtures thereof can be added. A fluorine-containing compound is also preferably included for its anti-caries activity. Suitable fluorine-containing compounds are NaF, Na-monofluorophosphate, KF, potassium monofluorophosphate, sodium fluorosilicate, sodium fluorozirconate, etc. (with NaF being most preferred). Finally, a foaming agent such as sodium lauryl sulfate (most preferred), sodium N-lauroyl sarcosinate, sodium coconut monoglyceride sulfonate, sodium N-methyl-N-palmitoyl lauride or a nonionic surfactant such as a polysorbate (e.g. Tween 60 or 80 manufactured by ICI Americas, Wilmington, Del.) or poloxamer or mixtures thereof, which also enhances the peroxide-bicarbonate-salt action, may be added. Flavoring agents, such as sodium saccharin, or other artificial sweeteners, peppermint or spearmint or other flavors are preferably added to further curb the unpleasant taste. Finally, methyl, butyl and/or propyl paraben, sodium benzoate, potassium sorbate or mixtures thereof are preferably added as preservatives, with methyl and propylparaben being most preferred. Use of a coloring agent is optional.

The constituents and quantities for the bicarbonate paste are as follows:

sodium bicarbonate: about 2–60% and preferably 20–40%;

salt: about 0–6%, preferably about 1–6% and most preferably about 2–4% of NaCl (preferred) or KCl, $MgCl_2$, $MgSO_4$, $Na_2SO_4$ or $K_2SO_4$ or mixtures thereof;

humectant: about 2–60% and preferably, 15–25% consisting of glycerin, sorbitol propylene glycol, polyethylene glycol, polypropylene glycol, ethoxylated or propoxylated lower fatty alcohols and mixtures thereof;

thickener-stabilizer: nonionic cellulose gum—about 0.1–5% and preferably 1.0–2.0%; or magnesium aluminum silicate or mixtures thereof in the same proportions;

stabilizer/polishing agent/cleanser: total about 1–30%, preferably about 1.5–20%; these preferably include one or more of: bentonite—about 0.5–7.5%; silica—about 0.1–8.0%; titanium dioxide—about 0.1–8.0%; and/or magnesium oxide—about 0.2–8.0%; preferably, about 1.5–5.0; 0.5–6.0; 0.5–3.0; and 0.5–3.0 percent, respectively.

fluorine-containing compound: sufficient to yield 200 to 3,000 ppm and preferably 1,000 to 2,000 ppm fluorine;

foaming agent: about 0.1-2.5%; preferably about 0.2-0.5%;

additional polishing agents: total about 1-30%, preferably about 5-20%;

flavoring agent(s): to taste, preferably 0.1-2%;

preservatives: about 0.05-0.5%.

The balance is purified water. A coloring agent may be added. The paste and the gel are preferably used in substantially equal proportions, by volume.

If urea peroxide is used in the gel, the bicarbonate paste composition does not change. The gel composition will be as follows:

urea peroxide: about 2-25%, preferably about 8-12%;

acrylic copolymer: about 0-3.5, preferably about 1-3%;

glycerin: balance.

The other polyols described above are reactive with the urea peroxide and should not be used.

The gel and paste combination may be simultaneously dispensed from separate collapsible tubes preferably made of plastic, or a plastic/metal laminate (to avoid reaction with $H_2O_2$) and enhanced flavor retention), such as tubes 1 and 2 shown in FIG. 1. The tubes are fitted with a Y-shaped conduit 3 which provides them with a common orifice 6. Conduit 3 may also be made of plastic (preferably by injection molding) and is preferably detachably but snugly attached to mouths 4,5 of tubes 1,2 so that it may be removed for cleaning. For additional convenience and in order to ensure dispensation of substantially equal amounts of the gel and paste, the tubes themselves may be held together, e.g., by banding or cementing, along corresponding dorsal sides, shown in FIG. 1, or, preferably, along corresponding ventral sides (see, e.g., FIG. 3A).

Alternatively, the two tubes may be constructed to have a common (preferably flat) sidewall portion 26 as shown in FIG. 2. In the latter case, the Y-shaped conduit may be unnecessary, if the mouths 24,25 of tubes 21,22 are sufficiently close so that sufficient quantities of the gel and paste may be simultaneously dispensed directly on the toothbrush. Conventional toothpaste or medicament tubes may be thus used after one of their side walls and the corresponding portion of their head structure are permanently deformed (e.g. by application of pressure) to a substantially flat surface.

A third alternative packaging method involves loading each of the gel and paste into separate compartments of the same collapsible tube, joined by a common orifice, as shown in FIG. 3. Composite tube 31 has compartments 32, 33 separated by divider 34 which is firmly attached along substantially diametrically opposed portions 35,36 of the sidewall 37, and corresponding portions 38,39 of head structure 40. Divider 34 may be glued or welded to sidewall 37 and head structure 40 of tube 31 during manufacture of the latter. Divider 34 is preferably provided with protruding portion 41, which extends into the mouth 42 of tube 31 until its edge is substantially flush with rim 43 of mouth 42. Thus, divider 34 forms with sidewall 37 two separate compartments 32,33 of substantially the same volume for storage of the gel and paste, respectively.

In another alternative packaging method, the two tubes are "concentric" as shown in FIG. 4A. Inner tube 401 lies within and parallel with outer tube 402.

Figure 4B:
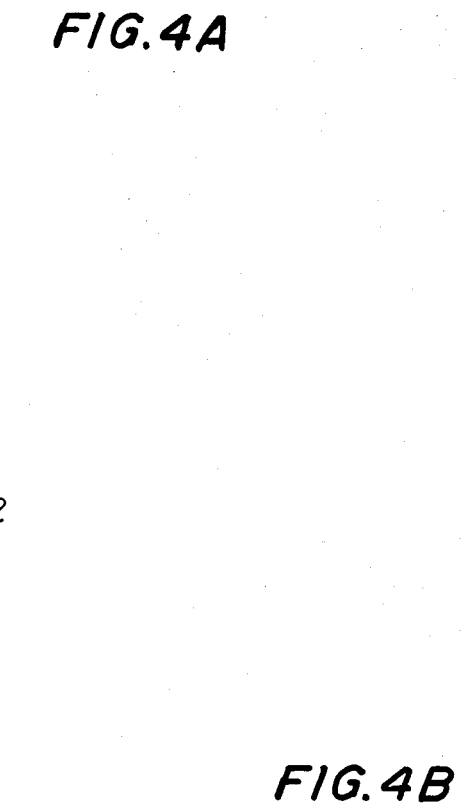

The mouths of the tubes 401 and 402, designated as 405 and 404 in FIG. 4, abut at the same point. Tube 401 is fastened on to tube 402 at the mouth by protrusion 406 (shown in enlargement in FIG. 4B, which is a cross-section of the embodiment of FIG. 4A taken along 4B—4B). Protrusions 406 are inserted in a groove of mouth 404 of tube 402. The material contained in tube 402 can still pass through the available space between mouth 404 of outer tube 402 and mouth 405 of inner tube 401. Engagement of pins 406 in the groove secures the inner tube 401 on the outer tube 402.

The closure 407 of the tube-within-a-tube (which can screw on the outer tube or simply be held by pressure) arrangement may but does not have to be equipped with an interior protrusion 408 to fit in the inner tube in order to prevent premature intermixing of the two components at the mouth of the tube. Because of the pseudoplastic quality of the gel and/or the memory of the plastic tube, however, such intermixing is not likely to occur. The tubes are filled from the bottom and are (subsequently) sealed together by conventional techniques.

Figure 5:
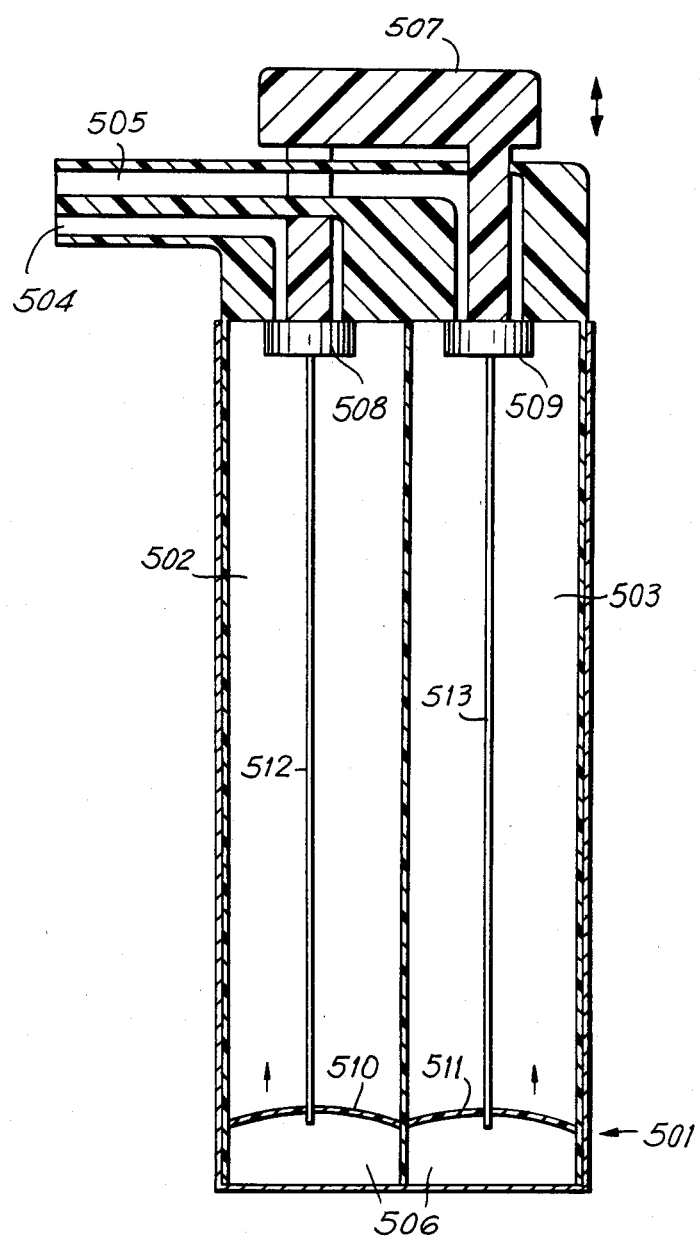
Figure 6:
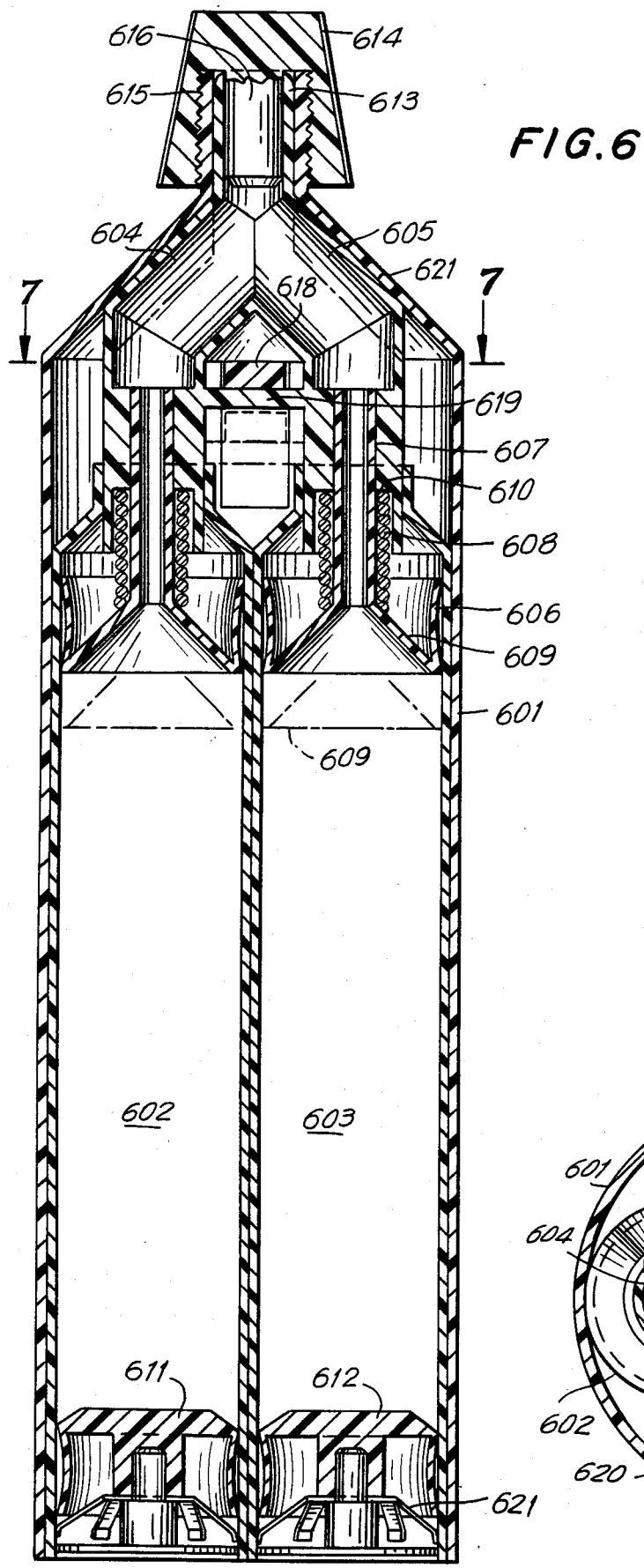

Other alternative packaging arrangements are disclosed in FIGS. 5 and 6. Pressurized container 501 in FIG. 5 is provided with two compartments 502 and 503 and two spouts 504 and 505. The internal pressure of the compartments is maintained by pressurized nitrogen, at the bottom 506 of each compartment. Operation of the mechanical actuator 507 (by pressing downwards) actuates valves 508 and 509 which release the contents of the compartments through the spouts (channels) causing the upwardly slidable sealing disks 510 and 511 (guided by members 512, 513) to move up along the compartments (due to the nitrogen being under pressure). Similar (but conventional) pressurized containers are manufactured for example by American Can Company. A dual compartment container, as described above, would be a modification of the existing containers.

Figure 7:
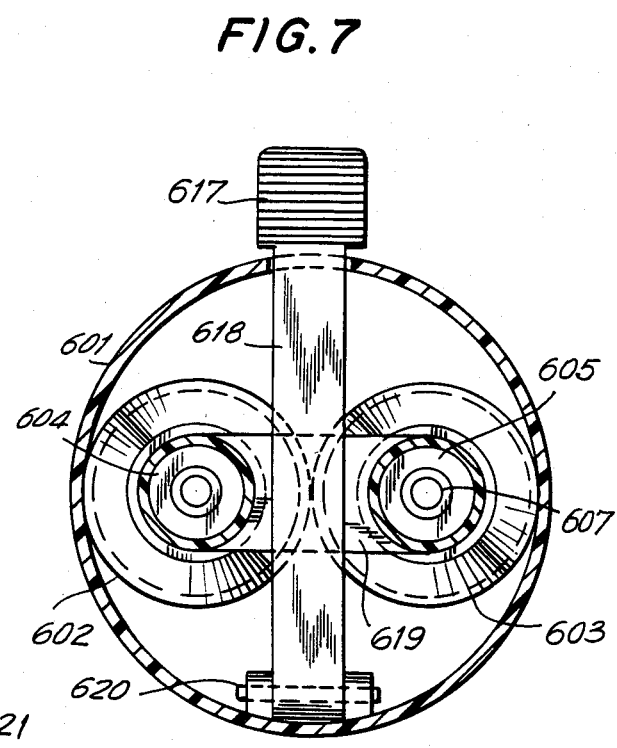

In an alternative pump embodiment depicted in FIGS. 6 and 7 a pressurized container 601 is provided with two compartments 602 and 603, and two spouts 604 and 605 for dispensing the gel and paste. Located within the tube 605 is a first piston 606 which is held in place by the upper surface of the contents within compartment 603 and a tubular extension 607 fitting within the lower portion of spout 605. A spring 608 is under compression and is held in position by the upper conical surface 609 of piston 606 and an inner shelf 610 of the spout 605. Lower pistons 611 and 612 are positioned within the lower portions of compartments 602 and 603 respectively so as to follow the dental material upwardly as it is being dispensed into the spouts 604 and 605 and eventually into nozzle 613. The upper part of container 601 has a reduced diameter to encircle the nozzle 613 and provide for a sliding engagement. Outer cap member 614 is threadedly engaged as at 615, with outer surface of nozzle 613 to effectively seal the container and prevent inadvertent dispensing of dental material as well as a pin 616 which fits snugly into open end of nozzle 613.

In operation, and with cap 614 removed, the user will depress a push button lever 617 (seen in FIG. 7) located outside the container 601. Lever 617 has substantially flat elongated member 618 which projects between spouts 604 and 605 and presses against wall 619 which bridges both spouts. Lever 617 is pivoted about pivot pin 620 affixed to inner wall of container 601. As lever 617 is depressed, member 618 will force spouts 604 and 605 downwardly and subsequently spring 608 as well as piston 606 will be lowered to phantom position (as seen in FIG. 6) causing dental material to flow upwardly within extension 607 and spout 605, mixing with material in spout 604 and through nozzle 613 to the bristles of a toothbrush. As the lever is released, the spring 608 will force nozzle 605 upwardly to its original position against conical portion 621 of container 601. The vacuum created will cause piston 606 to raise upwardly and concomitantly cause lower piston 612 to travel upwardly the distance of the expelled dental material. A spring clip 621 slideably engages inner surface of compartment 603 to allow piston to travel upwardly but be prevented from movement downwardly. Description of compartment 602 and spout 604 with its accompanying component parts operate in a like manner as described above.

The particular packaging arrangement used is not important. Those skilled in the art will be able to fashion several obvious modifications of the containers described herein by way of illustration.

Tubes, such as those suitable for use in accordance with the present invention are usually extruded around a cylindrical mandrel, cut into tube segments of suitable length, fitted with head structures and then filled from the bottom and pressed and/or welded closed, substantially as described in, e.g., U.S. Pat. No. 4,060,179 issued on Nov. 29, 1977 to McGhie, the disclosure of which is incorporated herein by reference.

In the case of the tube-within-a-tube embodiment of the present invention, the outer tube is provided first but it is not closed at the end opposite to that of the closure. The inner tube (also open-ended at the corresponding end) is inserted and fastened to the mouth of the outer tube. The two tubes are then filled and sealed together. A similar tube-within-a-tube arrangement has been proposed and described in U.S. Pat. No. 1,566,218 of Leland and issued on Dec. 15, 1925, incorporated here by reference.

The invention is further illustrated by the following specific examples which are designed merely to illustrate the present invention and not to limit its scope.

In these examples, a hydrogen peroxide gel containing 3–6.5% hydrogen peroxide by weight, useful for simultaneous administration with a sodium bicarbonate paste is prepared as follows:

EXAMPLE 1

Ingredients

| | |
|---|---|
| Hydrogen peroxide, 35% aqueous solution (5% $H_2O_2$ in final gel) | 14.3 parts |
| Purfied water | 84.45 |
| Copolymer of acrylic acid crosslinked with 1% by weight of polyallyl sucrose having 5.8 allyl groups per molecule (CARBOPOL 934 made by B. F. Goodrich Chemical Co., Akron, Ohio) | 0.5 |
| Hydroxyethyl cellulose | 0.5 |
| Triethanolamine | 0.25 |

The gel is prepared by combining the hydrogen peroxide solution with the purified water, followed by the gradual addition of CARBOPOL 934. Upon thorough dispersion of the copolymer hydroxyethyl cellulose is slowly added and dissolved. Finally, triethanolamine is added, forming a clear, homogeneous, stable and viscous gel having a pH of 3.4.

EXAMPLE 2

Ingredients

| | |
|---|---|
| Hydrogen peroxide, 35% aq. solution (3.5% $H_2O_2$ in final gel) | 10.0 parts |
| Distilled or deionized water | 88.9 |
| Acrylic acid copolymer CARBOPOL 940 (Goodrich) | 0.6 |
| Hydroxyethylcellulose | 0.5 |
| Sodium hydroxide, 10% solution | q.s. pH 3.8–4.0 |

Preparation: same as that of Example 1.

EXAMPLE 3

Ingredients

| | |
|---|---|
| Hydrogen peroxide, 35% (3.5% $H_2O_2$ in final gel) | 10.0 parts |
| Distilled or deionized water | 89.0 |
| Acrylic acid copolymer - CARBOPOL 941 (Goodrich | 0.7 |
| Hydroxypropylcellulose | 0.3 |
| Sodium hydroxide, 10% solution | q.s. pH 3.8–4.0 |

Preparation: same as that of Example 1.

EXAMPLE 4

Ingredients

| | |
|---|---|
| Hydrogen peroxide, 35% (4.0% $H_2O_2$ in final gel) | 11.5 parts |
| Distilled or deionized water | 86.65 |
| Acrylic acid copolymer - CARBOPOL 934 (Goodrich) | 0.75 |
| Sodium laurylsulfate, dentifrice grade | 0.50 |
| Hydroxypropylcellulose | 0.6 |
| Sodium hydroxide, 10% solution | q.s. pH 3.5–4.5 |

Preparation:
The hydrogen peroxide solution is combined with the distilled or deionized water. Sodium laurylsulfate is added under constant agitation and dissolved. Gradually, CARBOPOL 934 is added and dispersed. Hydroxypropylcellulose is added in increments and dissolved. When the mixture is homogeneous, sodium hydroxide is added slowly to the desired pH level and viscosity.

EXAMPLE 5

Ingredients

| | |
|---|---|
| Hydrogen peroxide, 35% (6.0% $H_2O_2$ in final gel) | 17.14 parts |
| Distilled or deionized water | 81.76 |
| Acrylic acid copolymer - CARBOPOL 940 (Goodrich) | 0.70 |
| Hydroxyethylcellulose | 0.40 |
| Sodium hydroxide, 10% solution | q.s. pH 3.5–4.0 |

Preparation: same as that of Example 1.

EXAMPLE 6

Ingredients

| | |
|---|---|
| Hydrogen peroxide, 35% (3.0% $H_2O_2$ in final gel) | 8.58 parts |
| Distilled or deionized water | 89.22 |
| Acrylic acid copolymer - CARBOPOL 934 | 0.70 |

-continued

| | |
|---|---|
| (Goodrich) | |
| Hydroxypropyl methylcellulose | 0.65 |
| Nonionic surfactant PLURONIC F 127 (BASF Corp., New Jersey) | 0.85 |
| Sodium hydroxide, 10% solution | q.s. pH 3.5–4.5 |

Preparation: same as that of Example 4.

EXAMPLE 7

The sodium bicarbonate paste is prepared as follows:

Ingredients

| | |
|---|---|
| Deionized water | 31.94 parts |
| Sorbitol 70% solution, USP | 20.0 |
| Cellulose gum - CMC 7MF. (Hercules) | 1.44 |
| Sodium saccharin | 0.20 |
| Magnesium aluminum (made by R. T. Vanderbilt Co., Inc., Norwalk, Conn.) | 1.17 |
| Sodium bicarbonate, fine powder | 40.00 |
| Sodium chloride | 4.00 |
| Sodium lauryl sulfate - dentifrice grade | 0.30 |
| Peppermint/Spearmint Flavor | 0.75 |
| Methylparaben, USP | 0.15 |
| Propylparaben, USP | 0.05 |

Procedure:
Glycerin and propylene glycol are combined in a first container with agitation. Cellulose gum is added and dispersed thoroughly throughout the mixture. Saccharin, methylparaben and propylparaben are added to the required amount of purified water in a separate container and heated to dissolve. VEEGUM is added and the mixture is agitated until uniform. The contents of the first container are slowly added to the second container and the final mixture is agitated thoroughly until uniform. Flavoring agent, sodium lauryl sulfate and coloring (if desired) are added and the paste is agitated at moderate speed until uniform. Entrapped air is removed by degassing in a vacuum vessel. Further homogeneity may be obtained by milling, if necessary.

EXAMPLE 8

Ingredients

| | |
|---|---|
| Deionized water | 33.43 parts |
| Glycerin | 10.00 |
| Propylene glycol | 10.0 |
| Cellulose gum - CMC 7MF (Hercules) | 1.45 |
| Sodium saccharin | 0.20 |
| Magnesium aluminum silicate - VEEGUM F | 1.17 |
| Sodium bicarbonate, fine powder | 25.00 |
| Dicalcium phosphate dihydrate | 13.50 |
| Dicalcium phosphate, anhydrous | 1.50 |
| Sodium chloride | 2.50 |
| Sodium lauryl sulfate, dentifrice grade | 0.30 |
| Methylparaben, USP | 0.15 |
| Propylparaben, USP | 0.05 |
| Peppermint/Spearmint Flavor | 0.75 |
| FD & C Blue No. 1, 0.1% solution | q.s. |
| DS & C Yellow No. 6, 0.1% | solution q.s. |

Procedure: Same as that of Example 8

EXAMPLE 9

Paste containing fluoride:

Ingredients

| | |
|---|---|
| Deionized water | 33.51 |
| Sorbitol, 70% solution | 20.00 |
| Sodium saccharin | 0.20 |
| Cellulose gum CMC 7MF (Hercules) | 1.54 |
| Magnesium aluminum silicate - VEEGUM F | 1.17 |
| Sodium fluoride | 0.33 |
| Methylparaben, USP | 0.15 |
| Propylparaben, USP | 0.05 |
| Calcium sulfate | 10.00 |
| Sodium bicarbonate | 25.00 |
| Sodium chloride | 2.00 |
| Hydrated aluminum oxide | 5.00 |
| Peppermint/Spearmint Flavor | 0.75 |
| Sodium lauryl sulfate | 0.30 |

Procedure: Same as that of Example 8.

EXAMPLE 10

Peroxide Gels

| Composition 10-A | |
|---|---|
| Hydrogen peroxide, 35% aqueous solution (4.0% $H_2O_2$ in final gel) | 11.5 |
| Distilled water | 86.6 |
| Acrylic acid copolymer - Carbopol 934 (Goodrich) | 1.5 |
| Sodium lauryl sulfate, dentifrice grade | 0.1 |
| Hydroxypropyl cellulose | 0.3 |
| Sodium hydroxide, 10% solution | q.s. pH 3.0–4.5 |

| Composition 10-B | |
|---|---|
| Hydrogen peroxide, 35% (4.0% $H_2O_2$ in final gel) | 11.5 |
| Distilled water | 88.0 |
| Acrylic acid copolymer (Carbopol 934, 940, 941, or 1342) | 1.5 |
| Sodium hydroxide, 10% solution | q.s. pH 3.0–4.5 |

| Composition 10-C | |
|---|---|
| Hydrogen peroxide, 35% (4.0% $H_2O_2$ in final gel) | 11.5 |
| Distilled water | 46.0 |
| Glycerin, anhydrous | 40.0 |
| Acrylic acid copolymer - Carbopol 941 | 2.5 |

Methods of preparation
Composition 10-A: same as listed in Example 4
Composition 10-B: same as in Example 4 except that sod. lauryl sulfate and hydroxypropyl cellulose were omitted. The composition including Carbopol 1342 has not been actually made.
Composition 10-C: The glycerin and water were combined and heated to 50°–60° C. Very slowly, Carbopol 941 was added under constant agitation.

When a clear gel had formed and no undissolved lumps remained, the gel was cooled to 25° C. and the hydrogen peroxide was added. Agitation was maintained until the mixture became homogeneous. The gel was de-aerated in a vacuum vessel.

EXAMPLE 11

Sodium bicarbonate Paste

| Composition 11-A | |
|---|---|
| Glycerin | 25.0 |
| Cellulose gum CMC 7MF (Hercules) | 1.54 |
| Deionized water | 32.71 |
| Magnesium aluminum silicate Veegum (R. T. Vanderbilt) | 1.10 |
| Sodium saccharin | 0.60 |
| Sodium chloride | 2.0 |
| Methylparaben | 0.15 |
| Propylparaben 0.05 | |
| (Sodium hydroxide solution 10%, q.s. pH 8.0–8.5, may be added, if necessary for pH adjustment) | |

| Composition 11-A | |
|---|---|
| Sodium fluoride | 0.22 |
| Bentonite | 4.0 |
| Titanium dioxide | 2.0 |
| Silica | 4.0 |
| Sodium bicarbonate | 25.0 |
| Flavor (spearmint) | 1.0 |
| Sodium lauryl sulfate | 0.3 |
| Color (FDC Blue No. 1) q.s. | |

Method of preparation

The cellulose gum was added to the glycerin and dispersed thoroughly.

In a separate vessel, the parabens, sodium saccharin, and sodium chloride were dissolved in water at 60°–70° C. To the clear solution was added the Veegum and the mixture was agitated until uniform. The pH of this solution was determined to be 8.0–8.5 (and adjusted, if necessary).

The gum dispersion was added to the Veegum solution and agitated until uniform.

To the blend were added the powders, bentonite, $TiO_2$, silica, $NaHCO_3$, and NaF, under vigorous agitation.

To the paste were added flavor, sodium lauryl sulfate and color.

The finished paste is milled and degassed in a vacuum vessel.

EXAMPLE 13

Urea peroxide gel

| Composition 13-A | | |
|---|---|---|
| Urea peroxide (35% $H_2O_2$ equivalent) | 10.0 | parts by weight |
| Glycerin, anhydrous | 90.0 | |

Method: Urea peroxide is slowly added under agitation to the anhydrous glycerin until a clear gel is formed which has a suitable consistency for filling into collapsible tubes.

| Composition 13-B | |
|---|---|
| Urea peroxide | 10.0 |
| Acrylic acid copolymers - Carbopol 941 | 1.5 |
| Glycerin, anhydrous | 88.5 |

The method is the same as that for 13-A except the urea peroxide and Carbopol 941 are both added to the glycerin solution.

Although the present invention has been described with reference to preferred embodiments, those of ordinary skill in the art will readily appreciate that many additions, deletions, modifications and substitutions are possible within the spirit of the present invention and the scope of the following claims.

What is claimed is:

1. A method for cleaning teeth comprising extruding a first semi-solid component comprising hydrogen peroxide as an active ingredient, said first component being suitable for oral use;
   extruding a second semi-solid component comprising sodium bicarbonate as an active ingredient, said second component being suitable for oral use;
   placing said first component and said second component in contact with each other on a toothbrush; and
   brushing said teeth using said first and second components concurrently as a cleaning medium.

2. The method of claim 1, wherein said first and second components are extruded together.

3. The method of claim 1, wherein said first and second components are extruded together on the toothbrush.

4. The method of claim 1, wherein said first and second components are extruded and placed on the brush separately.

5. The method of claim 1, wherein said brushing takes place immediately after extruding said components and placing them onto said toothbrush.

6. The method of claim 1, wherein said first component contains from about 0.1 to about 10 percent $H_2O_2$.

7. The method of claim 1, wherein said first component is a non-neutralized gel.

8. The method of claim 1, wherein said first component is a neutralized gel.

9. The method of claim 1, wherein said second component contains from about 2 to about 60 percent sodium bicarbonate by weight.

10. The method of claim 1, wherein said second component is a paste.

11. The method of claim 1, wherein said first component is a gel comprising as a gelling agent a member selected from the group consisting of (a) copolymers of acrylic acid cross-linked with polyallyl sucrose; (b) an organic polymeric acid colloid; and (c) a polyoxyethylene/polyoxypropylene block copolymer.

12. The method of claim 1, wherein said second component is a paste comprising a thickener/stabilizer.

13. The method of claim 12, wherein said paste component further comprises a bodying agent.

14. The method of claim 12, wherein said paste component further comprises an additional tooth-cleaning agent.

15. The method of claim 12, wherein said paste component further comprises a fluorine-containing compound having anti-caries activity.

16. The method of claim 7, wherein said gel component further comprises a copolymer of acrylic acid cross-linked with polyallyl sucrose as a gelling agent.

17. The method of claim 8, wherein said gel component further comprises a copolymer of acrylic acid cross-linked with polyallyl sucrose as a gelling agent and a polyol selected from the group consisting of glycerin, sorbitol, propylene glycol, polypropylene glycol, polyethylene glycol, an ethoxylated lower fatty alcohol and a propoxylated lower fatty acid alcohol.

* * * * *

US004687663B1

REEXAMINATION CERTIFICATE (3342nd)
United States Patent [19]
Schaeffer

[11] B1 4,687,663
[45] Certificate Issued  Oct. 7, 1997

[54] DENTAL PREPARATION, ARTICLE AND METHOD FOR STORAGE AND DELIVERY THEREOF

[75] Inventor: Hans A. Schaeffer, Linden, N.J.

[73] Assignee: Chesebrough Ponds USA Co., Greenwich, Conn.

Reexamination Request:
No. 90/003,665, Dec. 9, 1994

Reexamination Certificate for:
Patent No.: 4,687,663
Issued: Aug. 18, 1987
Appl. No.: 745,993
Filed: Jun. 17, 1985

Related U.S. Application Data

[63] Continuation-in-part of Ser. No. 737,157, May 23, 1985, abandoned, which is a continuation-in-part of Ser. No. 471,188, Mar. 1, 1983, Pat. No. 4,528,180.

[51] Int. Cl.$^6$ .................. A61K 7/16; A61K 7/18; A61K 7/20
[52] U.S. Cl. .................. 424/52; 424/49; 424/53; 514/835; 514/900; 514/902; 514/944; 222/1; 222/94
[58] Field of Search .................. 424/49–58

[56] References Cited

U.S. PATENT DOCUMENTS

| | | | |
|---|---|---|---|
| D. 315,496 | 3/1991 | Pettengill . | |
| 636,986 | 11/1899 | Heinen | 424/130 |
| 959,605 | 5/1910 | Queisser . | |
| 1,535,529 | 4/1925 | Hopkins . | |
| 1,566,218 | 12/1925 | Leland | 424/49 |
| 1,639,699 | 8/1927 | Hopkins . | |
| 1,699,532 | 1/1929 | Hopkins . | |
| 2,035,267 | 3/1936 | Fleischman | 424/53 |
| 2,054,742 | 9/1936 | Elbel . | |
| 2,124,971 | 7/1938 | Eisenberg et al. | 167/93 |
| 2,218,172 | 10/1940 | Kokatnur | 167/93 |
| 2,655,289 | 10/1953 | Peal | 222/162 |
| 2,724,385 | 11/1955 | Lockhart | 128/261 |
| 2,789,731 | 4/1957 | Marraffino . | |
| 2,819,723 | 1/1958 | Meyer | 132/116 |
| 2,826,339 | 3/1958 | Maillard | 222/137 |
| 2,830,730 | 4/1958 | Saffir . | |
| 2,905,364 | 9/1959 | Marraffino . | |
| 2,925,939 | 2/1960 | Spero . | |
| 2,959,327 | 11/1960 | Bloom . | |
| 3,166,221 | 1/1965 | Nielsen | 222/137 |
| 3,175,731 | 3/1965 | Ellman . | |
| 3,335,912 | 8/1967 | Reeves . | |
| 3,341,418 | 9/1967 | Moses et al. | 167/85 |
| 3,397,804 | 8/1968 | Delaney et al. | 424/52 |
| 3,499,844 | 3/1970 | Kibbel et al. . | |
| 3,574,824 | 4/1971 | Echeandia et al. . | |
| 3,577,521 | 5/1971 | Scheller et al. | 424/55 |
| 3,639,574 | 2/1972 | Schmolka . | |
| 3,651,931 | 3/1972 | Hsiung | 206/47 |
| 3,657,413 | 4/1972 | Rosenthal . | |
| 3,693,837 | 9/1972 | Yuhas . | |
| 3,747,804 | 7/1973 | Raaf et al. . | |
| 3,767,085 | 10/1973 | Cannon et al. | 222/82 |
| 3,874,558 | 4/1975 | Rockefeller | 222/92 |
| 3,881,529 | 5/1975 | Mannara . | |
| 3,907,991 | 9/1975 | Accetta | 424/130 |
| 3,935,304 | 1/1976 | Januszewski et al. . | |
| 3,935,305 | 1/1976 | Delaney et al. . | |
| 3,937,321 | 2/1976 | Delaney et al. . | |
| 3,937,803 | 2/1976 | Delaney et al. . | |
| 3,943,240 | 3/1976 | Delaney et al. | 424/49 |
| 3,952,782 | 4/1976 | Mannara . | |
| 3,952,920 | 4/1976 | Bergman | 222/137 |
| 3,966,863 | 6/1976 | Forward et al. | 424/52 |
| 3,977,826 | 8/1976 | Iscowitz | 8/10.2 |
| 3,980,767 | 9/1976 | Chown et al. | 424/52 |
| 4,046,288 | 9/1977 | Bergman | 222/135 |
| 4,060,179 | 11/1977 | McGhie | 222/92 |
| 4,098,435 | 7/1978 | Weyn . | |
| 4,121,739 | 10/1978 | Devaney et al. | 222/137 |
| 4,130,501 | 12/1978 | Lutz et al. . | |
| 4,160,022 | 7/1979 | Delaney et al. . | |
| 4,211,341 | 7/1980 | Weyn . | |
| 4,223,003 | 9/1980 | Scheller | 424/7 |
| 4,240,566 | 12/1980 | Bergman | 222/135 |
| 4,301,948 | 11/1981 | Czech et al. | 222/341 |
| 4,330,531 | 5/1982 | Alliger | 424/149 |

(List continued on next page.)

FOREIGN PATENT DOCUMENTS

| | | |
|---|---|---|
| 944506 | 4/1949 | France . |
| 2002622 | 7/1970 | Germany . |
| 1416782 | 12/1975 | United Kingdom . |
| 1492660 | 11/1977 | United Kingdom . |
| 1565672 | 4/1980 | United Kingdom . |
| 2112642 | 7/1983 | United Kingdom ............. A61K 7/16 |

OTHER PUBLICATIONS

Kirk–Othmer Encyclopedia of Chemical Technology Third Edition vol. 13 (1981) John Wiley & Sons, Inc. pp. 12–14 "Hydrogen Peroxide" (pH on p. 14).

Prevention 40(4):16 Apr. 1988 Stubborn Gum Disease—Antibiotics Keep It at Bay.

Foley Prevention 38(12):38–43 Dec. 1986 Block That Plaque Attack.

Freifeld Health 18(4):72 Apr. 1986 Attack on Plaque (cause of gum disease).

Gutfield Prevention 43(1):29 Jan. 1991 Feeding Your Smile (problems for teeth and gums).

Lyons Health 22(11):32–41 Dec. 1990 The Mid–Life Mouth Crisis.

(List continued on next page.)

*Primary Examiner*—Shep Rose
*Attorney, Agent, or Firm*—Pennie & Edmonds LLP; Milton L. Honig, Esq.

[57] ABSTRACT

Disclosed is a method for cleaning teeth including extruding a first semi-solid component including hydrogen peroxide as an active ingredient, and extruding a second semi-solid component comprising sodium bicarbonate as an active ingredient, the first and second components being suitable for oral use. The first component and the second component are placed in contact with each other on a toothbrush. The teeth are brushed using the first and second components concurrently as a cleaning medium.

U.S. PATENT DOCUMENTS

| | | |
|---|---|---|
| 4,431,631 | 2/1984 | Clipper et al. |
| 4,465,663 | 8/1984 | Schmolka |
| 4,487,757 | 12/1984 | Kiozpeuplov |
| 4,522,805 | 6/1985 | Gordon ............................ 424/52 |
| 4,528,180 | 7/1985 | Schaeffer |
| 4,533,069 | 8/1985 | Drobish .......................... 222/109 |
| 4,537,778 | 8/1985 | Clipper et al. .................. 424/53 |
| 4,547,362 | 10/1985 | Winston et al. ................. 424/49 |
| 4,623,536 | 11/1986 | Winston et al. ................. 424/49 |
| 4,663,153 | 5/1987 | Winston et al. ................. 424/52 |
| 4,687,663 | 8/1987 | Schaeffer |
| 4,742,940 | 5/1988 | Wilkinson ....................... 222/162 |
| 4,747,517 | 5/1988 | Hart .............................. 222/137 |
| 4,776,500 | 10/1988 | Ford |
| 4,849,213 | 7/1989 | Schaeffer |
| 4,964,539 | 10/1990 | Mueller |
| 4,983,379 | 1/1991 | Schaeffer |
| 5,020,694 | 6/1991 | Pettengill |
| 5,038,963 | 8/1991 | Pettengill et al. |
| 5,059,417 | 10/1991 | Williams et al. |

OTHER PUBLICATIONS

McVeigh Prevention 42(5):86–92 May 1990 Hi Tech Tooth Savers (12 Advanced Techniques That Control Gum Disease).
Shepherd FDA Consumer 24(4)8–13 May 1990 Brushing up on Gum Disease—What About Baking Soda?
Williams New England J. of Med. 322(6):373–382 Feb. 8, 1990 Medical Progress—Periodontal Disease.
Greene et al. JAMA 263(3):421–425 Jan. 19, 1990 Preventive Dentistry—Periodontal Diseases.
Zarrow Prevention 41(9):22 Sep. 1989 Better Than Brushing? Debate over a Special Treatment for Periodontal Disease Settled—a Tie!
Feverstein Current Health 15(5)28–29 Jan. 1989 Periodontal Disease—Nothing to Smile About—(Causes, Treatment).
Peters The Washington Post Jul. 16, 1986 T10, How Best to Save a Tooth? Periodontists are at Odds Over Merits of Surgery, The Medical Steps for Gum Disease.
The Washington Post Jul. 16, 1986 T11 Two Ways to Treat Gum Disease the Keyes Method.
Saturday Evening Post 258(3):30 Apr. 1986 Giving Plaque the Brush Off (gum disease).
Consumer Reports 51(3):144–169 Mar. 1986 Tooth Pastes—Tooth Paste Manufacturers Have Rediscovered Gum Disease.
Drake Philadelphia Inquirer Magazine Sun. Jun. 9, 1985 p. 17 The Dental Dilemma (gum disease).
Consumer Reports 49(3):138–141 Mar. 1984 Toothpastes (plain baking soda vs. baking soda toothpaste).
Herskowitz Philadelphia Inquirer Sun. Sep. 4, 1983 C01 Trying to Save Teeth Without Surgery (Keyes method).
Kotulak Miami Herald Wed Jan. 19, 1983 6E New Therapy May Reduce Gum Disease.
Weintraub Chicago Tribune Sun. Oct. 23, 1988 p. 8 Healthy Teeth Go Beyond a Smile Dentist Say Extra Work Needed to Fight Gum Disease.
Lunzer Forbes 141(12):300–302 May 30, 1988 "Tooth or Consequences" (gum disease).
Bluestone Business Week May 30, 1988 p. 101 "Worried About Losing Teeth?".
Jane Brody Sun Sentinel (FLA) Wed. Apr. 13, 1988 p. 3E Dental Discoveries Let the Buyer Beware Not All the Toothsome Claims Made by Various Product Mfrs. can be Realistically Taken at Face Value.
Jane Brody Detroit Free Press Fri. Feb. 12, 1988 p. 3C New Dental Products Abound but Old Ones Seem to Work Best.
Boffey The New York Times Thurs. Jan. 7, 1988 B12 col. 1 Health Dental Care Rebuilding Techniques Promise Broad Gains in Periodontal Fight.
Senz Saturday Evening Post 259(2):22–23 Mar. 1987 The Battle in Your Mouth (periodontal disease).
Pekkanen Reader's Digest 129(774):185–192 Oct. 1986 Do These Dentists Do Too Much? (Gum Disease—Keyes—vs. Dental Practice).
Haupt Working Woman Nov. 1991 16(11):pp. 140–147 "Six Hidden Problems You Can't Ignore" (gum disease).
Dewert & Glassman St. Louis Post Dispatch Sat. Sep. 7, 1991, p. 1D "Tooth Talk Column" (baking soda paste).
Jane Brody The New York Times Thurs. Oct. 18, 1990 Sect B p.12 col. 4 "Health Personal Health" (periodontal disease).
Hasselbring The Oregonian Mon. Jul. 9, 1990 Living Co3 Q&A. My Mother Suffered from Gum Disease.
Consumer Reports 54(8):504–509 Aug. 1989 New Ways to Save Your Teeth?
Graedon & Graedon St. Petersburg Times Sun. Dec. 3, 1989 2F People's Pharmacy (baking soda paste).
Kanner New York 21(43):16–20 Oct. 31, 1988 "Tartar Time" (gum disease).
USA Today 117(2521): 5 Oct. 1988 "Dentistry: Can You Avoid Plaque" (gum disease—brush & floss).
Russ J. Periodontology 54(3):181 Mar. 1983 Letter to the Editors.
Elder Modern Maturity Aug./Sep. 1980 31–32 An Alternative to Gum Surgery.
Caldwell et al. "A Textbook of Preventive Dentisty" pp. 189, 211 (1977) citing & footnoting Torell et al. (AA—with Reply Brief) Acta Odontol Scand. 23:287–312 (1965).
Keyes et al. Quintessence International 1:50–56 Jan. 1978 "Periodontics and Oral Hygeine".
"Periogene" Reg. T.M. 1350 230 First Used in Commerce Nov. 13, 1984 The First Marketed Twin Tube Baking Soda and Hydrogen Peroxide Toothpaste Keyes System.
"Gumbident" Reg. T.M. 1552 434 First Used in Commerce May 1, 1987 The Second Marketed Twin Tube Baking Soda and Hydrogen Peroxide Toothpaste Keyes' System.
"Perigel" Reg. T.M. 1724931 First Used in Commerce Jul. 1988 The Third Marketed Twin Tube Baking Soda and Hydrogen Peroxide Toothpaste Keyes' System.
"Mentadent" Reg. T.M. 1827994 and 1832568 First Used in Commerce Nov. 30, 1991 The Fourth Marketed Baking Soda and Hydrogen Peroxide (Separated) Keyes' System.
Chain Drug Review vol. 17 No. 4 Feb. 13, 1995 CDR—Special Report Technology Puts Benefits Back into Oral Care.
Trend is Toward Hydrogen Peroxide Formulas—New Ingredients Drive Toothpaste (See Table Best Selling Dentrifices 12 months thru Nov. 1994).
Chain Drug Review vol. 16 No. 20 Oct. 24, 1994 Sales of Toothpaste Rise Steadily—New Toothpaste Formulas Proliferate See: Best Selling Dentifrices 12 mos thru Nov. 19.
Jan. 26, 1983 Miami Herald Page 6E Harry Nelson "Technique No Cure All Dentist Says" Millions of Americans Believe That They Can Treat Their Gum and . . . Tooth Bone Disease by Brushing with Baking Soda Peroxide and Salt . . . .
Jan. 19, 1983 Miami Herald p. 6E Ronald Kotulak p. 6E "New Therapy May Reduce Gum Disease".
Jan. 16, 1983 Chicago Tribune Sect. 2 p. 9 Ronald Kotulak.
Feb. 14, 1983 People Weekly Frances MacLean v. 19 p. 57 "Dr. Paul Keyes Claims a Dental Breakthrough . . . ".
Jan. 17, 1983 U.S. News & World Report v. 94 p. 47 Alex Kucherov "Major Advances in Treating Your Teeth".

Feb. 11, 1983 Harper's Mar. 1983 pp. 23–24 David Owen "Gum Control" (Pub. Date Feb. 11, 1983).
Feb. 8, 1983 Black Enterprise Mar. 1983 13(8):82 Sandra Gregg "Keeping a Winning Smile" Pub. Date Feb. 8, 1983.
Oct. 1982 Mademoiselle p. 81 Karen Davis Watch Your Mouth.
Sep. 1982 Sci. Digest. 90:94 Ernest Newbrun "Baking Soda Curbs Gum Disease".
Aug. 1982 Glamour 80:22 C.R. Corcoran "5 Ways to Get a Prettier Smile".
Apr. 11, 1982 The New York Times Sect. 11 New Jersey p. 2, col. 1 Jane Wholey "Researchers Trying to Ease Toothache Pains".
Mar. 23, 1982 The New York Times Sect. C p. 1, col. 1 Jane Brody "Non Surgical Therapy for Gums Spurs Wide Debate".
1980–1981 Vogue Beauty Health Guide: 112, 165 Melva Weber "Better Teeth Than You Were Born With".
Dec. 7, 1981 Business Week 134, 135, 138 "New Ways to Keep Your Teeth".
Sep. 1981 MS 10(3):82–86 Devorkin, S "Don't Count on the Tooth Fairy".
Aug. 28, 1981 PR Newswire Mark Davidson "Shear Ignorance Threatens Your Teeth".
Apr. 12, 1981 The York Observer Kathy Haight Rock Hill Dentists Using Controversial Technique.
Nov. 29, 1980 The Economist p. 77 "Do You Want to Keep Your Teeth?".
Oct. 25, 1980 The Washington Post A9 Victor Cohn "Hill Study Hails Promising Cheaper Way to Treat Gum Disorders".
Aug.–Sep. 1980 Modern Maturity 31–32 Shirley Elder "An Alternative to Gum Surgery".
Aug. 25, 1980 Baltimore Evening Sun Sue Miller "Teeth, Old Practices May Mean Less Surgery".
Aug. 1980 Organic Gardening 27:112–Rebecca Christian "The Way to a Natural Smile".
Feb. 1980 Good Housekeeping 190:266 Schildkraut, M.C. "What Dentists Can Do Now".
Jan.–Feb. 1980 Mother Earth News p. 77 Robert Nara "Dental Medicine in Your Kitchen".
Jul. 1979 The Washingtonian pp. 90–91.
May 7, 1979 U.S. News & World Report p. 64 "Non–Surgical Gum Treatment".
Mar. 20, 1979 The Washington Post C1 B.D. Colen "Relief for Gums, Wallet: Less Painful Method Found for Treating Gums—Simpler Less Painful Treatment Draws Fire of Some Periodontists".
Jan. 21, 1979 The Washington Post C2 Judith Randal "Spare the Scalpel and Save the Gums: Regular Brushing with Baking Soda and Hydrogen Peroxide is a Sensible Alternative to Costly Painful Often Futile Gum Surgery".
Dec. 17, 1978 Daily News Dep. 17 Judith Randal "The Mouth That's Sore".
Mar. 29, 1982 New York 15:21 Bernice Kanner "The Selling of America—The Latest Toothpastes".
Apr. 1982 Technology Review: 79 L.P.C. "Rooting Out Tooth Rot".
Jun. 20, 1982 N.Y. Times Magazine 68–69 Deborah Blumenthal "Taking a Pasting".
Jul. 2, 1982 Science 217(4554): Dennis Leverett "Fluorides and the Changing Prevalence of Dental Caries".
Sep. 1982 Senior Scholastic 115:27 Holly Hughes "Save That Smile".
Oct. 1982 House and Garden 154(10):3436 165 Gale MacDonaldwood "Smile".
Mar. 1981 Good Housekeeping 192:6366 Alan Nourse "Complete Tooth Book".
Mar. 1981 Better Homes & Gardens 59(3):52–55, 58 Dan Kaercher "New Cost Cutting Dental Care Options".
Apr. 1981 Teen 25(4):39–40 "Sink Your Teeth into Good Health".
May 1981 Ladies Home Journal 37–38, 128 Gael MacDonaldwood "Keep Smiling: LHJ's Complete Guide to Preventive Dental Care".
Jun. 1981 World Health:15–18 Hend Gorchev "Fluorides Save Teeth".
Sep. 1981 Sciquest Carla Carson "The Fight Against Tooth Decay".
Jun. 1980 FDA Consumer 14:22–25 Annabel Hecht "Brushing and Rinsing to Prevent Cavities".
Feb. 1980 50 Plus:80–81 Carol & Damon Brennan "Are Your Teeth Getting the Brush-Off?".
Jan. 1979 Glamour 77:32+ There's a Lot of Good News in Dentistry.
Mar. 1979 Chemistry 52(3):12+ Harry Day Nutrition and Dental Health.
Feb. 1978 Good Housekeeping 186:210+ L. Banks "Commonsense Mouthcare".
Jun. 5, 1978 U.S. News & World Report 81–82 Daniel Scott.
Federal Register 44(214):63270–63285 Friday, Nov. 2, 1979.
A.D.A. 39th Ed. Jul. 1982 pp. 357–428 Accepted Dental Therapeutics.
A.P.H.A. Handbook of Non Prescription Drugs 7th Ed (1982), pp. 458–468.
Gold J. Periodont. 54:247 Apr. 1983.
A.D.A. 38th Ed. Sep. 1979 Accepted Dental Therapeutics pp. 262–281, 344–345, 316–317.
Remington's Pharmaceutical Sciences 16th Ed. (1980) pp. 732, 1892–1893, 346–348, 775 1229–1236, 725 1886, 1110, 739.
Martindale, The Extra Pharmacopoeia, 26th Ed. (1972) pp. 728–773, 1446–1451, 1704–1717.
The Merck Index, 9th Ed. (1976) pp. 633, 1109.
Federal Register 45(62):20666–20687 Friday Mar. 28, 1980.
Martindale The Extra Pharmacopoeia 28th Ed. (1982) pp. 700–703, 1232–1234, 633–644.
Federal Register 48(144):33984–33987 Tuesday Jul. 26, 1983.
Federal Register 50(189):39872–39873, 39854–39864 Monday Sep. 30, 1985.
Federal Register 51(138):26112–26114 Friday Jul. 18, 1986.
Federal Register 53(115):22430–22447 Wednesday Jun. 15, 1988.
Colgate Peak Baking Soda Toothpaste with Fluoride Carton Labels cite Delaney patents 3935304 3937803 pre-1983.
Synon Market Shares for Major Toiletries D&C1 Oct. 1974 pp. 36–39, 144–146 (note "Peak" in Toothpast Retail Market Share 1969–1973 on p. 39 Procter & Gamble Crest Gleem Colgate Palmolive Colgate Ultra Brite Peak Lever Brothers Close Up Pepsodent Aim & Carter Wallace Pearl Drops).
Aquafresh U.S. Reg. T.M. 1,006,821 Register Mar. 18, 1975 & Sec. 15 Affidavit.
Giges Advertising Age Jul. 30, 1979, pp. 3, 116.
The New York Times, Sep. 21, 1980 Sunday, Sec. 3 p. 21 col. 1.
Pat Sloan Advertising Age Feb. 7, 1994 p. 12.
Pat Sloan Chain Drug Review Aug. 15, 1994 p. 49.
A.P.H.A. Handbook of Non Prescription Drugs 10th Ed 1993 pp. 413–415, 809–812.
Brady et al Cosmetics & Toiletries 107:55–60 Mar. 1992.
Morton Pader Cosmetics & Toiletries 107:63–70 Mar. 1990.
A.P.H.A. Handbook of Non Prescription Drugs 8th Ed. (1986) pp. 477–505.
MentaDent Carton Labels (note patents listed).

Perigel Carton Labels (mentioned in remarks re: Litigation). A.D.A. Accepted Dental Therapeutics 40th Ed. Oct. 1984 pp. 395–421.

Goupil Chem. Abstracts, 87 #11477h) of Ger. Offen. No. 2,643,411, Apr. 7, 1977.

Keyes, et al., "The Use of Phase–Contrast Microscopy and Chemotherapy in the Diagnosis and Treatment of Periodontal Lesions–An Initial Report", 9 Quintessence International, 51–6 (Jan.

Salt, Soda and Hydrogen Peroxide . . . Is it Enough?, *Florida Dental Journal*, Summer 1981, vol. 52, No. 2, pp. 12–17, 48.

Ephraim, *Inorganic Chemistry*, Fourth Edition, Interscience Publishers, 1946, pp. 405–410.

Merck Index, Seventh Edition, 1960 p. 535.

*Textbook of Preventive Dentistry*, Fourth Edition, Saunders, 1977 p. 182.

"Market Shares for Major Toiletries", D&CI Oct., 1974, pp. 36, 39, 144.

"Dentifrice Battle On", Business Week, Oct. 14, 1939.

Teel Ad, Life Magazine, Jan. 12, 1942.

Orban, "Action of Oxygen on Chronically Inflamed Gingival Tissue", Journal of the American Dental Association, Nov. 1, 1942, pp. 2018–2025.

The Merck Index, Ninth Edition, 1976, pp. 214, 736, and 737.

*Industrial Gums*, Whistler, Ed., Second Edition, Academic Press 1973, pp. 98–99.

Keyes, "Measures To Aid In The Prevention and Control of Dental Caries and Periodontal Disease," Annotations From The International Dental Health Foundation, vol. 1, No. 1 (Jan. 1982).

Keyes et al., Annotations From The International Dental Health Foundation, vol. 1, No. 3 (Sep. 1982).

Cummings, Jr., A Periodontist's View on Surgical and Non–Surgical Therapy, Annotations From The International Dental Health Foundation, vol. 1, No. 2 (Jun. 1982).

Instructions and Treatment For Class I and II Periodontitis (Gum Disease).

Instructions and Treatment For Class III and IV Periodontitis (Gum Disease).

Torell, Per, et al., Two–Year Clinical Tests With Different Methods of Local Caries–Preventive Fluorine Application in Swedish School Children, *Acta Odont. Scand.*, 23:287–322, 1965.

Rundegren, J., et al., In Vivo and In Vitro Studies On a New Perioxide–Containing Toothpaste, *Scand. J. Dent. Res.*, 81(7):543–547, 1973.

Loesche, W., Chemotherapy of Dental Plaque Infections, *Oral Sci. Rev.*, 9(1):65–107, 1976.

Wennström, J., et al., Effect of Hydrogen Peroxide on Developing Plaque and Gingivitis in Man, *J. Clinical Periodontology*, 6(2):115–130, 1979.

Goldberg, H.J.V., et al., Effects of an Experimental Sodium Bicarbonate Dentifrice on Gingivitis and Plaque Formation: I. In Adults, *Clinical and Preventive Dentistry*, 5:12, 14, 16, 1979.

Schmid, R., et al., Effects of Topical Hydrogen Peroxide on Caries Incidence and Bacterial Agglomerate Formation in Rats, *J. Dental Research*, 59(7):1173, 1980.

Bayliss, C.E., et al., The Effect of Hydrogen Peroxide and Ultraviolet Irradiation on Non–Sporing Bacteria, *J. Applied Bacteriology*, 48:417–422, 1980.

Pitcher, G.R., et al., Access to Subgingival Plaque by Disclosing Agents Using Mouthrinsing and Direct Irrigation, *J. Clin. Periodontal.*, 7(4):300–308, 1980.

Saroff, S.A., et al., Sonicated and Passively Dispersed Hydrogen Peroxide in Periodontitis, *J. Periodont. Res.*, 15(2):216–222, 1980.

Simon, R.H., et al., Hydrogen Peroxide Causes the Fatal Injury to Human Fibroblasts Exposed to Oxygen Radicals, *J. Biol. Chem.*, 256(14):7181–7186, 1981.

DeRenzis, F.A., Endotoxin–Inactivating Potency of Hydrogen Peroxide: Effect on Cell Growth, *J. Dent. Res.*, 60(5):933–935, 1981.

Mühlemann, H.R., et al., Effect on Rat Caries of Endogenous and Exogenous Hydrogen Peroxide, *Caries Res.*, 15(1):46–53, 1981.

Waerhaug, J., Effect of Toothbrushing on Subgingival Plaque Formation, *J. Periodontal.*, 52(1):30–34, 1981.

Keyes, P.H., et al., Diagnosis of Creviculoradicular Infections: Disease–Associated Bacterial Patterns in Periodontal Lesions, *Host Parasite Interactions in Periodontal Diseases*, 395–403, 1982.

Keyes, P.H., et al., Microbial Community Structures as an Indicator of Therapeutic Progress in Treatment of Destructive Periodontitis, *J. Dent. Res.*, 61:314 No. 1224, 1982.

Fletcher, Paul, Keyes Approach in Periodontics, *NYS Dental Journal*, 48(5):284, 1982.

Scheffler, R.M., et al., Preventing and Treating Periodontal Disease With the Keyes Technique: A Preliminary Assessment, *Prev. Med.*, 11:677–695, 1982.

Firestone, A.R., et al., Effect of Topical Application of Urea Peroxide on Caries Incidence and Plaque Accumulation in Rats, *Caries Res.*, 16(2):112–117, 1982.

Wolff, L.F., et al., Phase Contrast Microscopic Evaluation of Subgingival Plaque in Combination With Either Conventional or Antimicrobial Home Treatment of Patients With Periodontal Inflammation, *J. Periodont. Res.*, 17(5):537–540, 1982.

Soh, L.L., et al., Effects of Subgingival Chlorhexidine Irrigation on Periodontal Inflammation, *J. Clin. Periodontal.*, 9(1):66–74, 1982.

Hardy, J.H., et al., Direct Irrigation and Subgingival Plaque, *J. Clin. Periodontal.*, 9(1):57–65, 1982.

Klein–Szanto, A.J., et al., Effects of Peroxides on Rodent Skin; Epidermal Hyperplasia and Tumor Promotion, *J. Invest. Dermatol.*, 79(1):30–34, 1982.

Cerra, M.B., et al., The Effect of Sodium Bicarbonate and Hydrogen Peroxide on the Microbial Flora of Periodontal Pockets; A Preliminary Report, *J. Periodontal.*, 53(10):599–603, 1982.

Low, S., et al., Comparison of Chemotherapy and Conventional Therapy Utilizing Phase Contrast Microscopy, *J. Dent. Res.*, 61 (Special Issue): 314, abstract No. 1223, 1982.

Felix, J.E., Letters to the Editor (Keyes Technique Questioned), *Ohio Dent. J.*, 56(11):17, 1982.

Weitberg, A.B., et al., Stimulated Human Phagocytes Produce Cytogenetic Changes in Cultured Mammalian Cells, *N. Engl. J. Med.*, 308(1):26–30, 1983.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is cancelled.

Claims 2 to 12 are determined to be patentable as amended.

Claims 13 to 17, dependent on an amended claim, are determined to be patentable.

New claims 18 to 28 are added and determined to be patentable.

2. The method of claim [1] *18*, wherein said first and second components are extruded together.

3. The method of claim [1] *18*, wherein said first and second components are extruded together on the toothbrush.

4. The method of claim [1] *18*, wherein said first and second components are extruded and placed on the brush separately.

5. The method of claim [1] *18*, wherein said brushing takes place immediately after extruding said components and placing them onto said toothbrush.

6. The method of claim [1] *18*, wherein said first component contains from about 0.1 to about 10 percent $H_2O_2$.

7. The method of claim [1] *18*, wherein said first component is a non-neutralized gel.

8. The method of claim [1] *18*, wherein said first component is a neutralized gel.

9. The method of claim [1] *18*, wherein said second component contains from about 2 to about 60 percent sodium bicarbonate by weight.

10. The method of claim [1] *18*, wherein said second component is a paste.

11. The method of claim [1] *18*, wherein said first component is a gel comprising as a gelling agent a member selected from the group consisting of (a) copolymers of acrylic acid cross-linked with polyallyl sucrose; (b) an organic polymeric acid colloid; and (c) a polyoxyethylene/polyoxypropylene block copolymer.

12. The method of claim [1] *18*, wherein said second component is a paste comprising a thickener/stabilizer.

*18. A method for cleaning teeth by applying an active oxygen aqueous cleaning medium to teeth and gums in the buccal cavity comprising*

*extruding a first semi-solid component comprising hydrogen peroxide as an active ingredient, said first component being suitable for oral use;*

*extruding a second semi-solid component comprising sodium bicarbonate as an active ingredient, said second component being suitable for oral use, one of said semi-solid components being flavored;*

*placing said components in contact with each other on a toothbrush; and*

*brushing said teeth and gums using said components concurrently as the active oxygen aqueous cleaning medium and thereby evolving active oxygen when the brush is applied to the teeth and gums where mixing of said components takes place,*

*the semi-solid consistency of both of said components rendering them sufficiently stable and firm to remain in place on the toothbrush until application to the teeth and gums,*

*said semi-solid components being contained in a dual compartment article for storage and delivery which prevents contact between hydrogen peroxide and sodium bicarbonate prior to placement thereof on a toothbrush, said article including means for dispensing controlled quantities of said semi-solid components from said article by applying pressure on said components from slideably moving members activated by user operation of said means,*

*and, at the same time, the effervescence accompanying release of active oxygen from immediate mixing of the two components, when the brush is applied to the teeth and gums, enables said flavor to produce a pleasant taste in the mouth which overcomes the unpleasant taste of the mixture of hydrogen peroxide and sodium bicarbonate.*

*19. The method of claim 14 wherein said additional tooth-cleaning agent is calcium sulfate, calcium phosphate, hydrated aluminum oxide, calcium carbonate, magnesium carbonate, magnesium silicate or mixtures thereof.*

*20. The method of claim 18 wherein said second component includes a flavoring agent curbing the unpleasant taste of hydrogen peroxide and sodiumn bicarbonate.*

*21. The method of claim 20 wherein said flavoring agent is an artificial sweetener.*

*22. The method of claim 20 wherein said flavoring agent is sodium saccharin.*

*23. The method of claim 18 wherein said flavor is an artificial sweetener.*

*24. The method of claim 23 wherein said sweetener is sodium saccharin.*

*25. The method of claim 18 wherein the structural means includes an actuator means operation of which by the user enables application of force effective to expel said semi-solid components, out of the article upon a toothbrush.*

*26. The method of claim 18 wherein said article has dual compartments, each containing one of said first and second semi-solid components, said dispensing means being effective to apply simultaneous pressure upon both said semi-solid components.*

*27. A method for cleaning teeth by applying an active oxygen aqueous cleaning medium to teeth and gums in the buccal cavity comprising*

*extruding a first semi-solid component comprising hydrogen peroxide as an active ingredient, said first component being suitable for oral use;*

*extruding a second semi-solid component comprising sodium bicarbonate as an active ingredient, said sec-* ond component being suitable for oral use, one of said semi-solid components being flavored;

placing said components in contact with each other on a toothbrush; and brushing said teeth and gums using said components concurrently as the active oxygen aqueous cleaning medium and thereby evolving active oxygen when the brush is applied to the teeth and gums where mixing of said components takes place, the semi-solid consistency of both of said components rendering them sufficiently stable and firm to remain in place on the toothbrush until application to the teeth and gums, said semi-solid components being contained in a dual compartment article for storage and delivery which prevents contact between hydrogen peroxide and sodium bicarbonate prior to placement thereof on a toothbrush, said article including means for dispensing controlled quantities of said semi-solid components from said article by pumping action activated by user operation of said means.

28. A method for cleaning teeth by applying an active oxygen aqueous cleaning medium to teeth and gums in the buccal cavity comprising:

extruding a first semi-solid component comprising hydrogen peroxide as an active ingredient, said first component being suitable for oral use;

extruding a second semi-solid component comprising sodium bicarbonate as an active ingredient, said second component being suitable for oral use;

placing said components in contact with each other on a toothbrush; and brushing said teeth and gums using said components concurrently as the active oxygen aqueous cleaning medium and thereby evolving active oxygen when the brush is applied to the teeth and gums where mixing of said components takes place, the semi-solid consistency of both of said components rendering them sufficiently stable and firm to remain in place on the toothbrush until application to the teeth and gums, said semi-solid components being contained in a dual compartment article for storage and delivery which prevents contact between hydrogen peroxide and sodium bicarbonate prior to placement thereof on a toothbrush, said article including means for dispensing controlled quantities of said semi-solid components from said article by pumping action activated by user operation of said means.

* * * * *